United States Patent
Vu

(10) Patent No.: US 11,579,127 B2
(45) Date of Patent: Feb. 14, 2023

(54) APPARATUS, METHOD, AND SYSTEM FOR INDICATION OF AN OXIDATIVE TREATMENT

(71) Applicant: ASP Global Manufacturing GmbH, Schaffhausen (CH)

(72) Inventor: Roger Vu, Irvine, CA (US)

(73) Assignee: ASP Global Manufacturing GmbH, Schaffhausen (CH)

( * ) Notice: Subject to any disclaimer, the term of this patent is extended or adjusted under 35 U.S.C. 154(b) by 809 days.

(21) Appl. No.: 16/437,753

(22) Filed: Jun. 11, 2019

(65) Prior Publication Data

US 2020/0003740 A1 Jan. 2, 2020

Related U.S. Application Data

(60) Provisional application No. 62/692,278, filed on Jun. 29, 2018.

(51) Int. Cl.
| | |
|---|---|
| *G01N 31/22* | (2006.01) |
| *A61L 2/18* | (2006.01) |
| *A61L 2/28* | (2006.01) |
| *G01N 21/17* | (2006.01) |
| *G01N 21/78* | (2006.01) |

(Continued)

(52) U.S. Cl.
CPC ............ *G01N 31/226* (2013.01); *A61L 2/186* (2013.01); *A61L 2/28* (2013.01); *G01N 21/17* (2013.01); *G01N 21/78* (2013.01); *A61L 2209/211* (2013.01); *G01N 2021/1738* (2013.01);

(Continued)

(58) Field of Classification Search
CPC ...... G01N 31/226; G01N 21/17; G01N 21/78; G01N 2021/1738; G01N 2021/3125; G01N 2021/773; A61L 2/186; A61L 2/28; A61L 2209/211
See application file for complete search history.

(56) References Cited

U.S. PATENT DOCUMENTS

| 8,802,392 B2 * | 8/2014 | Chandrapati | ......... C12M 23/32 |
| | | | 435/31 |
| 2002/0151084 A1 * | 10/2002 | Lippold | ............... G01N 31/223 |
| | | | 436/163 |

(Continued)

FOREIGN PATENT DOCUMENTS

| EP | 0914833 A2 | 5/1999 |
| EP | 2253334 A1 | 11/2010 |
| JP | 2005233839 A | 9/2005 |

OTHER PUBLICATIONS

International Search Report and Written Opinion for PCT/IB2019/000818, dated Dec. 16, 2019.

*Primary Examiner* — Jennifer Wecker
*Assistant Examiner* — Alea N. Martin
(74) *Attorney, Agent, or Firm* — K&L Gates LLP

(57) ABSTRACT

An indicator and method of use thereof, and indicator system and method of use thereof are provided to determine the degree of an oxidative treatment. An indicator is incorporated into the oxidative treatment. The object and the indicator are subjected to the oxidative treatment. A discoloration of the indicator occurs based on an oxidation of the polymer by a process condition of the oxidative treatment oxidizing the polymer. The discoloration of the indicator is measured against a threshold color value to determine the degree of the oxidative treatment.

17 Claims, 2 Drawing Sheets

(51) Int. Cl.
  *G01N 21/31* (2006.01)
  *G01N 21/77* (2006.01)
(52) U.S. Cl.
  CPC ............... *G01N 2021/3125* (2013.01); *G01N 2021/773* (2013.01)

(56) References Cited

U.S. PATENT DOCUMENTS

| | | | |
|---|---|---|---|
| 2004/0225162 | A1 | 11/2004 | Sunkara et al. |
| 2006/0286627 | A1* | 12/2006 | Bochner ............ G01N 33/5023 435/40.5 |
| 2007/0054412 | A1* | 3/2007 | Cregger .................. C09B 21/00 436/166 |
| 2009/0220378 | A1* | 9/2009 | McDonnell .......... H05H 1/2406 422/400 |
| 2015/0004706 | A1* | 1/2015 | Nair .......................... A61L 2/28 436/1 |

* cited by examiner

APPARATUS, METHOD, AND SYSTEM FOR INDICATION OF AN OXIDATIVE TREATMENT

CROSS REFERENCE TO RELATED APPLICATIONS

This application claims the benefit of U.S. Provisional Application Ser. No. 62/692,278 filed Jun. 29, 2018 which is hereby incorporated by reference.

FIELD

The present disclosure relates to an indicator, and a method of use thereof, and an oxidative treatment system and method of use thereof. In various examples, the present disclosure relates to indication of a degree of an oxidative treatment of an object.

BACKGROUND

Various medical devices are used in numerous procedures in the medical field. These devices are as varied as the procedures themselves. After a medical device, such as an endoscope, is used, the medical device is treated (e.g., cleaned, disinfected, and/or sterilized) in order to prepare the medical device for its next use. The treatment may include placing the medical device in a sterilizer and exposing the medical device to a sterilant. One popular type of sterilizer is the STERRAD® brand of sterilizers manufactured by Advanced Sterilization Products, of Irvine, Calif., a division of Ethicon, Inc. of Somerville, N.J. The STERRAD® sterilizer can house one or more removable trays that fit within a sterilization chamber. Each tray may be filled with medical devices such as a scalpel, an endoscope, scissors, and the like. To sterilize the medical devices, the sealed chamber is exposed to a vacuum and an oxidative chemical such as, hydrogen peroxide, is introduced into the sterilization chamber. Ensuring the medical devices are sterilized prior to use on a patient can prevent the risk of cross contamination and the spread of disease.

SUMMARY

In one aspect, a method for determining a degree of an oxidative treatment of an object is provided. The method comprises incorporating an indicator comprising a polymer into the oxidative treatment. The object and the indicator are subjected to the oxidative treatment. A discoloration of the indicator occurs based on an oxidation of the polymer by a process condition of the oxidative treatment oxidizing the polymer. The discoloration of the indicator is measured against a threshold color value to determine the degree of the oxidative treatment.

In another aspect, a method for determining a degree of an oxidative treatment of an object is provided. The method comprises incorporating an indicator into the oxidative treatment. The indicator comprises a polymer comprising at least one group selected from an amine, a methylene, and a methine. The object and the indicator are subject to the oxidative treatment. A discoloration of the indicator occurs based on an oxidation of the polymer by a process condition of the oxidative treatment oxidizing the polymer. The discoloration of the object at least partly occurs through oxidization of the group to form a quinone. The discoloration of the indicator is measured against a threshold color value by measuring at least one of an absorption and a reflection of electromagnetic radiation by the indicator at a wavelength of 400 nm to 700 nm to determine the degree of the oxidative treatment.

In yet another aspect, an indicator for determining a degree of an oxidative treatment is provided. The indicator comprises a polymer comprising at least one group selected from an amine, a methylene, and a methine. The group is suitable to oxidation responsive to exposure to an oxidative chemical in the oxidative treatment. The oxidation of the group discoloring the indicator.

In a further aspect, a system for determining a degree of an oxidative treatment of an object is provided. The system comprises an indicator, a chamber, and a color value device. The indicator comprises a polymer suitable to discoloration based on an oxidation of the polymer by a process condition of the oxidative treatment oxidizing the polymer. The chamber is suitable to receive an object and the indicator. The chamber is suitable to subject the object and the indicator to the oxidative treatment including the process condition. The color value device is suitable to determine the discoloration of the indicator against a threshold color value.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description taken in conjunction with the accompanying drawings, wherein.

Corresponding reference characters indicate corresponding parts throughout the several views. The exemplifications set out herein illustrate certain embodiments, in one form, and such exemplifications are not to be construed as limiting the scope of the examples in any manner.

DETAILED DESCRIPTION

Figure 1:
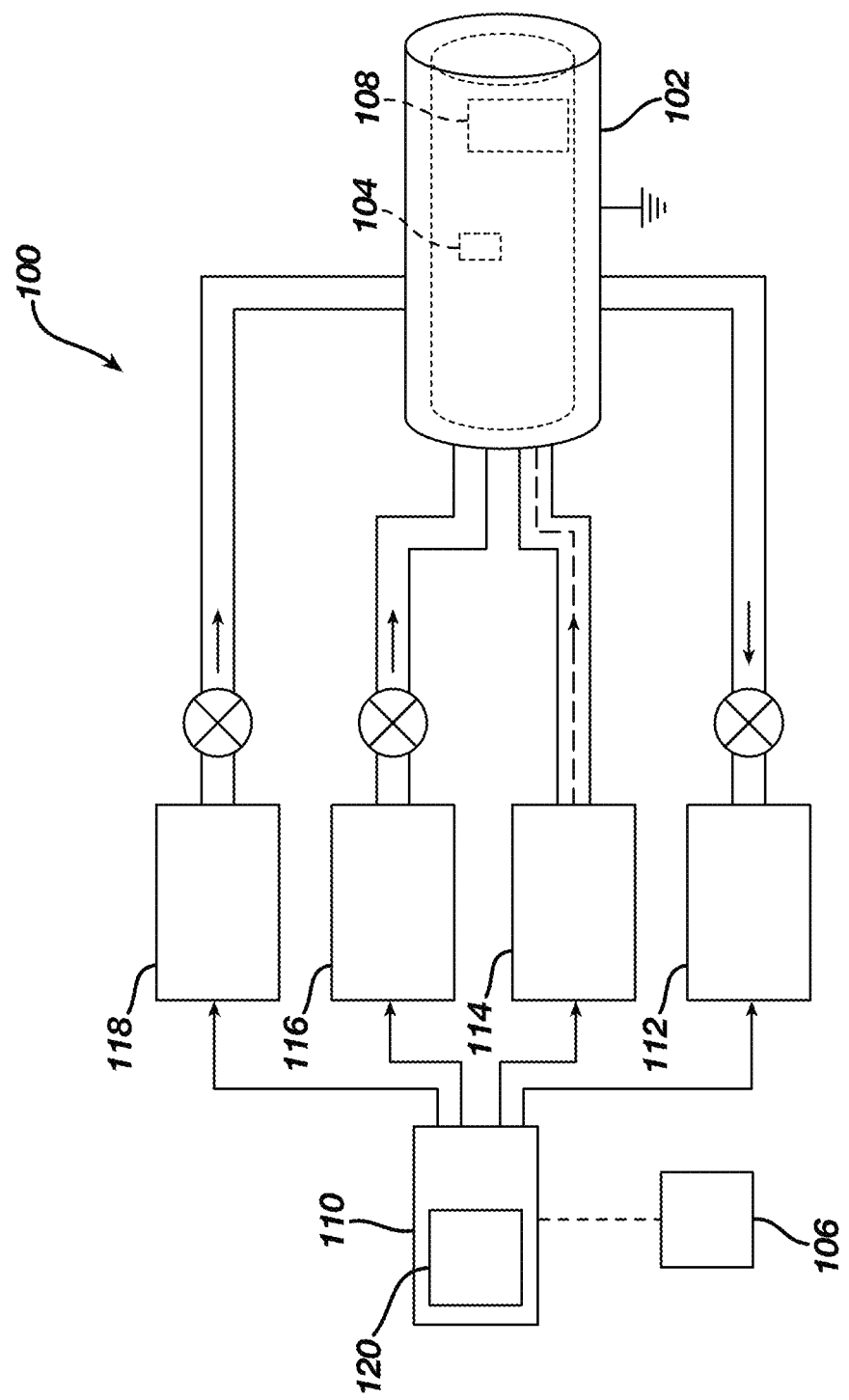
FIG. 1 is schematic view of a non-limiting example of a treatment system according to the present disclosure.

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification such that amending to expressly recite any such sub-ranges would comply with the requirements of 35 U.S.C. § 112 and 35 U.S.C. § 132(a).

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

As used in this specification, the term "polymer" means prepolymers, oligomers, and both homopolymers and copolymers.

An object can undergo a treatment process to prevent cross-contamination and the spread of disease. As used herein, a "treatment process" may be a cleaning process, a disinfecting process, a sterilization process, the like, and combinations thereof. A treatment process may be either manual, automated, or some combination thereof, and may utilize a treatment agent. As used herein, a "treatment agent" can comprise at least one of a cleaning agent, a disinfectant, and a sterilant. As used herein a "cleaning process" means a treatment process employing a cleaning agent that removes and/or eliminates debris such as, for example, a dirt, a dust, a particle, an oil, a protein, a carbohydrate, and the like. As used herein, a "cleaning agent" means a type of treatment agent that removes and/or eliminates debris during a cleaning process such as, for example, a surfactant and/or a detergent.

A disinfecting process and a sterilization process can remove and/or eliminate a bioburden from an object. A bioburden may be, for example, a bacterium (e.g., *mycobacterium*, bacterial spores), an archaeon, a eukaryote, a virus, a fungus, and/or other forms of biological agents. Bacterial spores (e.g., endospores) are a form of bacteria which are dormant and highly resistive to physical and chemical degradation. As used herein, a "disinfecting process" means a treatment process that substantially removes a bioburden except for bacterial spores. As used herein, "substantially remove" means that at least 99% of the bioburden has been removed from the object such as, for example, at least 99.9% of the bioburden, at least 99.99% of the bioburden, at least 99.999% of the bioburden, or at least 99.9999% of the bioburden has been removed from the object. As used herein, a "sterilization process" means a treatment process which substantially removes a bioburden including bacterial spores. The sterilization process may include, for example, the addition of heat, freezing, a sterilant, irradiation, pressure, and combinations thereof. The sterilant may comprise a chemical capable of sterilization. The disinfection process may include, for example, the addition of heat, a disinfectant, irradiation, pressure, and combinations thereof. The disinfectant may comprise a chemical capable of disinfection.

As used herein, an "oxidative treatment" is meant to mean a treatment process which includes exposing an object to an oxidative chemical. A cleaning process, a disinfecting process, and/or a sterilization process can comprise an oxidative treatment. For example, a cleaning agent, a disinfectant, and/or a sterilant can comprise an oxidative chemical. The oxidative chemical can comprise, for example, hydrogen peroxide, nitrogen oxide, ozone, peracetic acid, chlorine, iodine, and combinations thereof. In various examples, the oxidative chemical can comprise hydrogen peroxide such as, for example, at least 10 percent by weight, at least 20 percent by weight, at least 30 percent by weight, at least 40 percent by weight, at least 50 percent by weight, or at least 60 percent by weight, at least 70 percent by weight, at least 80 percent by weight, at least 90 percent by weight, or 99 percent by weight hydrogen peroxide. In various examples, the oxidative chemical comprises hydrogen peroxide and a balance of water.

Process indicators, such as chemical indicators, are used in many processes as a diagnostic tool to indicate whether a desired process or reaction has taken place. In the medical industry, chemical indicators can be used in a sterilization system to visually indicate whether a sterilization process has taken place. For example, many medical devices must be sterilized prior to use on a patient. Thus, device manufacturers often sterilize instruments before providing them to medical facilities, and medical facilities generally have their own sterilization systems to sterilize instruments prior to use on a patient to ensure sterility.

Chemical indicators can be defined into six types in accordance with ISO 11140-1:2014. Type 1 chemical indicators can indicate a binary result that an object has been exposed to a process condition of a treatment process or that the object has not been exposed to the process condition of the treatment process. Thus, Type 1 chemical indicators can only indicate the gross failure of a treatment process.

However, determining that a treatment process was only partially performed can be desired in order to ensure an object is substantially free of bioburden and ready for the next use. Thus, an indicator and method of use thereof, and indicator system and method of use thereof are provided to determine the degree of an oxidative treatment that an object was exposed to. In various examples, the indicator can determine a degree of a process condition of the oxidizing treatment.

The indicator can comprise a polymer which can be suitable to oxidation responsive to a process condition of the oxidative treatment. The process condition can be one or more process parameter used during the oxidative treatment that exposes the polymer to an oxidative chemical, such as exposure time and/or exposure concentration. In various examples, the polymer can comprise at least one group selected from an amine, a methylene, and a methine. The group can be suitable to oxidation responsive to the process condition. The polymer can comprise at least one of polyurethane and epoxy. In various examples, the polymer can comprise an aromatic polymer. In various examples, the indicator can be transparent and/or colorless prior to exposure to an oxidative treatment, and in other examples the indicator can be white prior to exposure to an oxidative treatment. The description of the color is for illustration purposes only and the color of the polymer prior to exposure to an oxidative treatment may be different.

Regardless of the initial color, the indicator can become discolored based on the oxidation of the polymer. For example, a change in an absorption and/or a reflection of electromagnetic radiation by the indicator can occur. The change in absorption and/or reflection can be at a wavelength of 400 nm to 700 nm such as, for example, 550 nm to 600 nm or 570 nm to 590 nm. In various examples, the color of the indicator can be yellow responsive to the oxidation of the polymer. Thus, the degree of discoloration of the indicator can correspond to the degree of oxidation of the indicator. For example, depending on the degree of oxidation of the polymer, the color of the indicator can be, for example, various shades of yellow.

The discoloration of the indicator can be based on the oxidation of the group in the polymer. For example, the discoloration may at least partly occur through oxidation of the amine, oxidation of the methylene, and/or oxidation of the methine. The oxidation of the polymer of the indicator can be suitable to form a quinone. A non-limiting example of an oxidation of a polymer comprising polyurethane is provided in Schemes 1-3.

Scheme 1

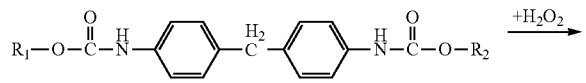

Scheme 2

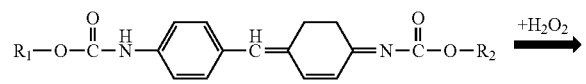

Scheme 3

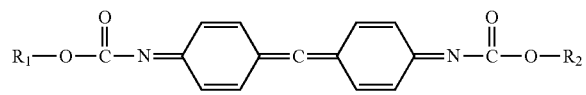

$R_1$ and $R_2$ may be an additional polymer unit as known in the art. In Scheme 1, a polyurethane polymer comprising methylene diphenyl diisocyanate (MDI) is exposed to hydrogen peroxide, in examples where the oxidative treatment employs hydrogen peroxide as the oxidative chemical. The hydrogen peroxide oxidizes the central alkyl group (e.g., methylene) and a first amine adjacent to a phenyl group to form a monoquinone-imide as shown in Scheme 2. The monoquinone-imide is exposed to hydrogen peroxide as shown in Scheme 2. The hydrogen peroxide oxidizes the central alkyl group (e.g., methine) and a second amine adjacent to the phenyl group to form a diquinone-imide as shown in Scheme 3. Accordingly, the oxidation of the amine, the methylene, and/or the methine in the polymer of the indicator can be suitable to form a quinone.

A quinone can be an aromatic compound and can have an absorption at a wavelength of 400 nm to 700 nm such as, for example, 550 nm to 600 nm or 570 nm to 590 nm. In various examples, the quinone can comprise a quinone-imide such as, for example, monoquinone-imide and diquinone-imide. An increase in oxidation of the group can result in an increase in formation of the quinone in the polymer resulting in an increase in absorption in a wavelength range of 400 nm to 700 nm such as, for example, 550 nm to 600 nm or 570 nm 590 nm. Thus, the degree of discoloration of the indicator can correspond to the degree of oxidation of the indicator. The degree of oxidation of the polymer in the indicator can be based on the exposure concentration and/or exposure time of the indicator to an oxidative chemical. In various examples, the indicator may be a Type 5 indicator according to ISO 11140-1:2014. For example, the indicator can be equivalent to, or exceed, the performance requirements in ISO 11138 for biological indicators.

A method is provided herein for determining a degree of an oxidative treatment of the object. More specifically, the indicator can be incorporated into an oxidative treatment of the object. The object and the indicator can be subjected to the oxidative treatment including a process condition. The process condition can comprise exposing the object and the indicator to an oxidative chemical at a sufficient exposure concentration and for a sufficient exposure time to achieve treatment of the object such as, for example, remove and/or eliminate bioburden. In various examples, the process condition of the oxidative treatment can comprise an exposure to hydrogen peroxide at an exposure concentration of at least 2 mg/L, such as for example at least 2.3 mg/L or at least 6 mg/L. In various examples, the process condition of oxidative treatment can comprise exposure to hydrogen peroxide for an exposure time of at least 5 minutes such as, for example, at least 10 minutes, at least 30 minutes, or at least 1 hour.

Discoloration of the indicator can occur based on oxidation of the polymer by the process condition of the oxidative treatment that oxidizes the polymer, and in various examples, the discoloration of the indicator can at least partly occur through oxidization of at least one group selected from an amine, a methylene group, and a methine. The oxidation of the group can form a quinone. The indicator may be discolored based on a change in the absorption and/or reflection of electromagnetic radiation by the indicator. For example, the absorption and/or the reflection of the indicator can change in a wavelength range of 400 nm to 700 nm such as, for example, 550 nm to 600 nm or 570 nm to 590 nm. In various examples, the polymer in the indicator changes to a shade of yellow.

The discoloration of the indicator can be measured against a threshold color value to determine the degree of oxidative treatment. In various examples, the indicator can be measured against a plurality of threshold color values. Discoloration of the indicator can be measured by measuring the absorption and/or reflection of electromagnetic radiation by the indicator. For example, the absorption and/or reflection of electromagnetic radiation by the indicator can be measured at a wavelength in the range of at 400 nm to 700 nm such as, for example, 550 nm to 600 nm or 570 nm to 590 nm. In various examples, the discoloration is measured utilizing a color value device and/or through visual observation of the indicator. When a color value device is utilized to measure the discoloration, the color value device can comprise, for example, at least one of a spectrometer, a colorimeter, and a color chart. For example, the absorbance or transmittance of the indicator may be measured utilizing a spectrometer.

The threshold color value can be an absolute measurement of the absorbance and/or the reflection the indicator. For example, the threshold color value may be an absorbance value or a transmittance value of the indicator at a wavelength in the wavelength range of 400 nm to 700 nm. The threshold color value may be a value in the International Commission on Illumination L*a*b* (CIELAB) color space, which expresses color as three numerical values L*, a*, and b*. An L* value, an a* value, and/or a b* value of an indicator can be measured by a spectrophotometer and/or by capturing a photo of the indicator and analyzing the captured photo. For example, a photo can be captured with a digital camera and an L* value, an a* value, and/or a b* value can be measured from the captured photo utilizing analysis software such as Adobe Photoshop, available from Adobe Inc., San Jose, Calif., United States. In various examples, the threshold color value can be a value for a change in measurement of the absorbance and/or the reflection of the indicator after exposure to an oxidative treatment compared to before the oxidative treatment.

In various examples, a visual observation of the indicator can be made to measure the discoloration. For example, the visual color of the polymer of the indicator can indicate the degree of oxidative treatment to which the indicator has been exposed during the oxidative treatment. The visual color of the polymer may then be compared to a color chart to determine the degree of the oxidative treatment.

The measured discoloration can be used to determine the degree of oxidative treatment. For example, the measured discoloration can indicate the degree of oxidation of the polymer in the indicator which can be a result of exposure to an oxidative chemical. The degree of oxidation of the polymer in the indicator can be based on the exposure concentration and/or the exposure time to the oxidative chemical. Thus, the indicator can be incorporated into an oxidative treatment process in order to determine the degree of an oxidative treatment to which the indicator and the object were exposed to during the oxidative treatment which then can be used to determine the degree of disinfection or sterilization of the object.

As illustrated in FIG. 1, a treatment system 100 for determining a degree of an oxidative treatment of an object 108 is provided. The system 100 comprises a chamber 102, and an indicator 104, a color value device 106. The chamber 102 can be suitable to receive the object 108 to be treated and the indicator 104. The chamber 102 can be suitable to subject the object 108 and the indicator 104 to an oxidative treatment under various process conditions. For example, the chamber 102 can be suitable to clean, disinfect, and/or sterilize the object 108. The object 108 can comprise a medical device such as, for example, a scalpel, an endoscope, scissors, and the like. In various examples, the object 108 can comprise the indicator 104. For example, the object 108 can comprise a housing comprising the indicator 104, the object 108 can comprise a window comprising the indicator 108, and/or a tag comprising the indicator can be operatively coupled to the object 108.

The color value device 106 can comprise, for example, a spectrometer, a colorimeter, and a color chart. In various examples comprising a spectrometer and/or a colorimeter, the color value device 106 can output an absorbance value and/or a reflectance value which can be manually compared to a threshold color value and/or automatically compared to a threshold color value to determine the degree of oxidative treatment to which the indicator 104 and object 108 have been exposed.

In various examples, a processor 110 can be provided that is operatively coupled to memory 120 and in communication with the color value device 106 to determine the discoloration of the object 108. For example, the processor 110 can receive the measurement from the color value device 106 and compare the measurement to the threshold color value. In various examples, the threshold color value is stored in memory 120. Based on the comparison, the processor 110 can determine the degree of the oxidative treatment achieved during the treatment process. For example, the processor 110 can determine the discoloration is greater than or equal to a threshold color value. The degree of discoloration can correspond to the degree of oxidative treatment of the indicator 104 and thus, the degree of oxidative treatment of the object 108. In various examples, when the discoloration of the indicator 104 is greater than or equal to a threshold color value, the object 108 has been sterilized and the object 108 can be substantially free from bioburden. In various examples where the object 108 comprises the indicator 104, the degree of discoloration can be an aggregate degree of discoloration. For example, the aggregate degree of discoloration can be based on an aggregate of oxidative treatments to which the object 108 has been exposed. The aggregate degree of discoloration may be used to determine the age of the object 108, the operational life of the object 108 remaining, and/or that the object 108 should no longer be used.

In various examples, the processor 110 can be in communication with each of the components of the system 100 that are in communication with the chamber 102 such that the processor 110 can control each component. The processor 110 can control the system 100 based on the measurement of the discoloration of the indicator 104. For example, the processor 110 may end the oxidative treatment when the discoloration of the indicator 104 is greater than or equal to the threshold color value indicating that the object 108 has been sterilized.

In various examples, the system 100 comprises a vacuum pump 112, a radio frequency (RF) generator 114, a dispenser 116, and a vent 118. The vacuum pump 112 and vent 118 can be in fluid communication with the chamber 102 and the vacuum pump 112 and the vent 118 can be suitable to control a pressure of the chamber 102. The RF generator 114 can be in communication with the chamber 102 and can generate a plasma utilizing RF energy. The term "plasma" is intended to include any portion of the gas or vapor that contains electrons, ions, free radicals, dissociated and/or excited atoms, and/or molecules produced as a result of an applied electric field, including any accompanying radiation that might be produced.

An oxidative treatment can be performed in the following manner schematically illustrated by system 100 in FIG. 1. The object 108 can be placed in the chamber 102, the chamber 102 can be closed, and the pressure in the chamber 102 can be reduced, for example, by vacuum pump 112. An oxidative chemical of, for example, hydrogen peroxide, can be injected and vaporized by dispenser 116 and provided to the chamber 102 so that the oxidative chemical diffuses onto the object 108 and indicator 104. The pressure in the chamber 102 can be reduced and the oxidative chemical can be left in contact with the object 108 and the indicator 104 for a period of time to remove bioburden on the object 108.

A plasma can be initiated by applying RF energy from RF generator 114. In the plasma, the oxidative chemical can be disassociated into reactive species that collide/react with and reduce and/or eliminate bioburden. In various examples, the plasma can convert residual hydrogen peroxide into water and oxygen. The plasma can be maintained for a sufficient time to achieve treatment such as, for example, sterilization of the object 108. The RF energy from the RF generator 114 can be turned off, the vacuum can be released, and the chamber 102 can be returned to atmospheric pressure by the introduction of filtered air through vent 118. In general, plasma can be used to remove residual oxidative chemical and can enhance sterilization efficacy.

The indicator according to the present disclosure can determine a degree of an oxidative treatment such as, for example, a STERRAD® sterilization process, in a treatment system such as, for example, a STERRAD® hydrogen peroxide gas plasma type sterilizer. It is to be appreciated that the indicator is not limited to uses associated with the STERRAD® sterilization process. Instead, the indicator may find use in a plurality of applications including plasma sterilization processes. The STERRAD® sterilization process should be viewed as exemplary of the plurality of applications.

Example

Figure 2:
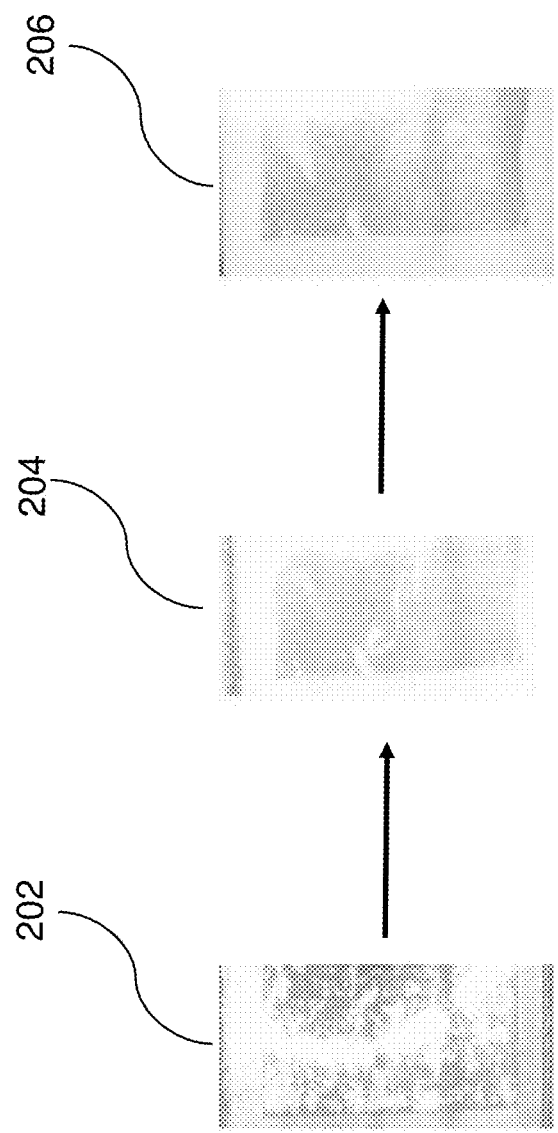
FIG. 2 is photographs of the discoloration of a non-limiting example of an indicator comprising a polyurethane polymer according to the present disclosure.

The discoloration of an indicator comprising a polyurethane polymer was tested. Referring to FIG. 2, an initial photo 202 of the indicator and a control object was taken. Analysis of the initial photo 202 was performed in Adobe Photoshop, and the initial b* color value of the indicator in the photo 202 was measured to be 8. The indicator and the control object were placed in a STERRAD® 100NX sterilizer manufactured by Advanced Sterilization Products, of Irvine, Calif., a division of Ethicon, Inc. of Somerville, N.J. The indicator and the control object were treated in a STERRAD® sterilization process in the sterilizer for 90 minutes. The oxidative chemical utilized in the sterilization process was hydrogen peroxide vapor at a concentration of 15 mg/L.

The color of the indicator was observed after each sterilization cycle. The indicator began discoloring upon subjecting the indicator to the sterilization process (e.g., absorption in a wavelength range of 550 nm to 600 nm as evidenced by the yellow color). It is believed that the yellow color of the indicator could be detected after a single cycle utilizing a spectrometer and/or a colorimeter. After 8 cycles of the sterilization process, a visible yellow color of the indicator could be observed as shown in photo 204. Analysis of the photo 204 was performed in Adobe Photoshop, and the b* color value of the indicator in the photo 204 was measured to be 14 which is an increase of 6 compared to the photo 202.

After 50 cycles, a significant yellow color of the indicator could be observed as shown in photo 206. Analysis of the photo 206 was performed in Adobe Photoshop. The b* color value of the indicator in the photo 206 was measured to be 59 which is an increase of 51 compared to the photo 202 and an increase of 45 compared to the photo 204. For each photo, the b* color value was averaged over a 1 inch by 5 inch area of the raw image. The yellow color of the indicator increased after each successive sterilization cycle demonstrating a correlation between the yellow color of the indicator and the degree of oxidative treatment (e.g., sterilization) that the indicator has undergone (e.g., exposure to hydrogen peroxide). Thus, measuring the discoloration of the indicator can be used to determine the exposure concentration and/or exposure time of the indicator and object to an oxidative chemical such as hydrogen peroxide. Other polymers are also believed to have an according discoloration responsive to oxidation in an oxidative treatment.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various examples have been described herein, many modifications, variations, substitutions, changes, and equivalents to those examples may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed examples. The following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the invention according to the present disclosure include, but are not limited to, the aspects listed in the following numbered clauses.

1. A method for determining a degree of an oxidative treatment of an object, the method comprising:
   incorporating into the oxidative treatment an indicator, the indicator comprising a polymer;
   subjecting the object and the indicator to the oxidative treatment, a discoloration of the indicator occurring based on an oxidation of the polymer by a process condition of the oxidative treatment oxidizing the polymer; and
   measuring the discoloration of the indicator against a threshold color value to determine the degree of the oxidative treatment.
2. The method of clause 1, wherein the polymer further comprises a group selected from an amine, a methylene, and a methine.
3. The method of clause 2, wherein the discoloration of the indicator at least partly occurs through oxidization of the group.
4. The method of clause 3, wherein the oxidizing of the group comprises forming a quinone.
5. The method of clause 4, wherein the quinone comprises a quinone-imide.
6. The method of any one of clauses 1 to 6, wherein the discoloration of the indicator comprises changing at least one of absorption and reflection of electromagnetic radiation by the indicator.
7. The method of any one of clauses 1 to 6, wherein the changing of the at least one of the absorption and the reflection of the electromagnetic radiation by the indicator is at a wavelength of 400 nm to 700 nm.
8. The method of any one of clauses 1 to 7, wherein the measuring of the discoloration comprises measuring at least one of an absorption and a reflection of electromagnetic radiation by the indicator.
9. The method of clause 8, wherein the measuring at least one of the absorption and the reflection of the electromagnetic radiation by the indicator is at a wavelength of 400 nm to 700 nm.
10. The method of any one of clauses 1 to 9, wherein the measuring of the discoloration comprises utilizing a color value device.
11. The method of any one of clauses 1 to 10, wherein the measuring of the discoloration comprises a visual observation of the indicator.
12. The method of any one of clauses 1 to 11, wherein the polymer comprises at least one of polyurethane and epoxy.
13. The method of any one of clauses 1 to 12, wherein the indicator prior to the oxidative treatment is transparent.
14. The method of any one of clauses 1 to 13, wherein the indicator is a Type 5 chemical indicator.
15. The method of any one of clauses 1 to 14, wherein the oxidative treatment comprises at least one of cleaning, disinfecting, and sterilizing.
16. The method of any one of clauses 1 to 15, wherein the oxidative treatment comprises at least one of disinfecting and sterilizing.
17. The method of any one of clauses 1 to 16, wherein the object is sterilized when the discoloration of the indicator is greater than the threshold color value.
18. The method of any one of clauses 1 to 17, wherein the process condition of the oxidative treatment is an exposure to an oxidative chemical.
19. The method of clause 18, wherein the oxidative chemical is hydrogen peroxide.
20. The method of clause 19, wherein the process condition of the oxidative treatment is an exposure to hydrogen peroxide of greater than or equal to 2 mg/L.
21. The method of any one of clauses 1 to 20, wherein the object comprises a medical device.
22. A method for determining a degree of an oxidative treatment of an object, the method comprising:
   incorporating into the oxidative treatment an indicator, the indicator comprising a polymer comprising at least one group selected from an amine, a methylene, and a methine;
   subjecting the object and the indicator to the oxidative treatment, a discoloration of the indicator occurring based on an oxidation of the polymer by a process condition of the treatment oxidizing the polymer, the discoloration of the indicator at least partly occurs through oxidization of the group to form a quinone; and
   measuring the discoloration of the indicator against a threshold color value by measuring at least one of an absorption and a reflection of electromagnetic radiation by the indicator at a wavelength of 400 nm to 700 nm to determine the degree of the oxidative treatment.
23. An indicator for determining a degree of an oxidative treatment, the indicator comprising:
   a polymer comprising at least one group selected from an amine, a methylene, and a methine, the group suitable to oxidation responsive to exposure to an oxidative chemical in the oxidative treatment, the oxidation of the group discoloring the indicator.
24. The indicator of clause 23, wherein the discoloration comprises a change in at least one of an absorption and a reflection of electromagnetic radiation by the indicator at a wavelength of 400 nm to 700 nm.
25. The indicator of any one of clauses 23 and 24, wherein the polymer comprises at least one of polyurethane and epoxy.
26. A system for determining a degree of an oxidative treatment of an object, the system comprising:
   an indicator comprising a polymer suitable to discoloration based on an oxidation of the polymer by a process condition of the oxidative treatment oxidizing the polymer;

a chamber suitable to receive an object and the indicator, the chamber suitable to subject the object and the indicator to the oxidative treatment including the process condition; and a color value device suitable to determine the discoloration of the indicator against a threshold color value.

27. The system of clause 26, wherein the polymer comprises at least one group selected from an amine, methylene, and methine.

28. The system of clause 27, wherein the process condition is suitable to oxidize the group.

29. The system of any one of clauses 26 to 28, further comprising:
a processor operatively coupled to memory and in communication with the color value device to determine the discoloration of the indicator is greater than or equal to a threshold color value.

30. The system of any one of clauses 26 to 29, wherein the threshold color value device comprises at least one of a spectrometer, a colorimeter, and a color chart.

31. The system of any one of clauses 26 to 30, wherein the polymer comprises at least one of polyurethane and epoxy.

32. The system of any one of clauses 26 to 31, wherein the chamber is suitable to at least one of clean, disinfect, and sterilize the object.

33. The system of any one of clauses 26 to 32, wherein the chamber is suitable to at least one of disinfect and sterilize the object.

34. The system of any one of clauses 26 to 33, wherein the chamber is suitable to sterilize the object.

35. The system of any one of clauses 26 to 34, wherein the object comprises a medical device.

In summary, numerous benefits have been described which result from employing the concepts described herein. The foregoing description of the one or more examples has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various embodiments and with various modifications as are suited to the particular use contemplated. It is intended that the claims submitted herewith define the overall scope.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A method for determining a degree of an oxidative treatment of an object, the method comprising:
incorporating into the oxidative treatment an indicator, the indicator comprising a polymer;
subjecting the object and the indicator to the oxidative treatment, a discoloration of the indicator, including the polymer, occurring based on an oxidation of the polymer by a process condition of the oxidative treatment oxidizing the polymer; and
measuring the discoloration of the indicator against a threshold color value to determine the degree of the oxidative treatment.

2. The method of claim 1, wherein the polymer further comprises a group selected from an amine, a methylene, and a methine.

3. The method of claim 2, wherein the discoloration of the indicator at least partly occurs through oxidization of the group.

4. The method of claim 3, wherein the oxidizing of the group comprises forming a quinone.

5. The method of claim 4, wherein the quinone comprises a quinone-imide.

6. The method of claim 1, wherein the measuring of the discoloration comprises measuring at least one of an absorption and a reflection of electromagnetic radiation by the indicator.

7. The method of claim 6, wherein the measuring at least one of the absorption and the reflection of the electromagnetic radiation by the indicator is at a wavelength of 400 nm to 700 nm.

8. The method of claim 1, wherein the measuring of the discoloration comprises utilizing a color value device.

9. The method of claim 1, wherein the measuring of the discoloration comprises a visual observation of the indicator.

10. The method of claim 1, wherein the polymer comprises at least one of polyurethane and epoxy.

11. The method of claim 1, wherein the indicator prior to the oxidative treatment is transparent.

12. The method of claim 1, wherein the indicator is a Type 5 chemical indicator.

13. The method of claim 1, wherein the oxidative treatment comprises at least one of cleaning, disinfecting, and sterilizing.

14. The method of claim 1, wherein the object is sterilized when the discoloration of the indicator is greater than the threshold color value.

15. The method of claim 1, wherein the process condition of the oxidative treatment is an exposure to an oxidative chemical.

16. The method of claim 15, wherein the oxidative chemical is hydrogen peroxide.

17. The method of claim 1, wherein the object comprises a medical device.

* * * * *